United States Patent
Tsukamoto et al.

(10) Patent No.: US 9,882,247 B2
(45) Date of Patent: *Jan. 30, 2018

(54) LITHIUM ION BATTERY CAPABLE OF BEING DISCHARGED TO ZERO VOLTS

(71) Applicant: Quallion LLC, Sylmar, CA (US)

(72) Inventors: Hisashi Tsukamoto, La Canada, CA (US); Clay Kishiyama, San Mateo, CA (US); Mikito Nagata, Saugus, CA (US); Hiroshi Nakahara, Santa Clarita, CA (US); Tiehua Piao, Valencia, CA (US)

(73) Assignee: Quallion LLC, Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/987,923

(22) Filed: Sep. 16, 2013

(65) Prior Publication Data

US 2015/0074987 A1 Mar. 19, 2015
US 2017/0125838 A9 May 4, 2017

Related U.S. Application Data

(60) Continuation of application No. 11/978,081, filed on Oct. 25, 2007, now Pat. No. 8,535,831, which is a continuation of application No. 10/217,967, filed on Aug. 13, 2002, now Pat. No. 7,993,781, which is a division of application No. 09/675,287, filed on Sep. 29, 2000, now Pat. No. 6,596,439.

(60) Provisional application No. 60/199,895, filed on Apr. 26, 2000.

(51) Int. Cl.
*H01M 4/00* (2006.01)
*H01M 10/058* (2010.01)
*A61N 1/378* (2006.01)
*H01M 4/66* (2006.01)
*H01M 4/131* (2010.01)
*H01M 4/133* (2010.01)
*H01M 10/0525* (2010.01)

(52) U.S. Cl.
CPC .......... *H01M 10/058* (2013.01); *A61N 1/378* (2013.01); *H01M 4/131* (2013.01); *H01M 4/133* (2013.01); *H01M 4/661* (2013.01); *H01M 4/662* (2013.01); *H01M 10/0525* (2013.01); *Y02E 60/122* (2013.01); *Y02P 70/54* (2015.11); *Y10T 29/4911* (2015.01); *Y10T 29/49108* (2015.01)

(58) Field of Classification Search
CPC ....................................... H01M 4/00
See application file for complete search history.

(56) References Cited

U.S. PATENT DOCUMENTS

| 6,159,636 | A  * | 12/2000 | Wang | C01G 45/1221 429/223 |
| 6,596,439 | B1 * | 7/2003  | Tsukamoto et al. | 429/245 |
| 7,101,642 | B2 * | 9/2006  | Tsukamoto et al. | 429/245 |
| 7,993,781 | B2 * | 8/2011  | Tsukamoto et al. | 429/248 |

(Continued)

*Primary Examiner* — Jacob Marks
(74) *Attorney, Agent, or Firm* — Gabrilovich, Dodd & Lindsey LLP (57) ABSTRACT

A lithium ion battery particularly configured to be able to discharge to a very low voltage, e.g. zero volts, without causing permanent damage to the battery. More particularly, the battery is configured to define a Zero Volt Crossing Potential (ZCP) which is lower than a Damage Potential Threshold (DPT).

25 Claims, 7 Drawing Sheets

(56) References Cited

U.S. PATENT DOCUMENTS 8,535,831 B2 * 9/2013 Tsukamoto et al. .......... 429/225
8,637,184 B2 * 1/2014 Tsukamoto et al. ....... 429/218.1

* cited by examiner

|     | Positive Active Material | Negative Substrate Material | Temperature | Result |
|-----|--------------------------|------------------------------|-------------|--------|
| (1) | $LiCoO_2$ | Copper | 25 °C | Fail; 79.9% Retention |
|     |          |        | 37 °C | Fail; 76.2% Retention |
| (2) | $LiCoO_2$ | Titanium | 25 °C | Pass; 98.6% Retention |
|     |          |          | 37 °C | Fail; 73.5% Retention |
| (3) | $LiNi_{0.8}Co_{0.2}O_2$ | Copper | 25 °C | --- |
|     |                          |        | 37 °C | Fail; 90% Retention |
| (4) | $LiNi_{0.8}Co_{0.2}O_2$ | Titanium | 25 °C | --- |
|     |                          |          | 37 °C | Pass; 98.8% Retention |

LITHIUM ION BATTERY CAPABLE OF BEING DISCHARGED TO ZERO VOLTS

RELATED APPLICATIONS

This application is a continuation of U.S. patent application Ser. No. 11/978,081, filed on Oct. 25, 2007, entitled Lithium-Ion Battery Capable of Being Discharged to Zero Volts; U.S. patent application Ser. No. 11/978,081 is a continuation of U.S. patent application Ser. No. 10/217,967, filed on Aug. 13, 2002, entitled Method for Making a Lithium-Ion Battery Capable of Being Discharged to Zero Volt, now issued as U.S. Pat. No. 7,993,781; which is a divisional of U.S. patent application Ser. No. 09/675,287, filed Sep. 29, 2000, entitled Lithium-Ion Battery Capable of being discharged to Zero Volts, now issued as U.S. Pat. No. 6,596,439 B1; which claims the benefit of U.S. Provisional Application 60/199,895 filed Apr. 26, 2000; each of which is incorporated herein in its entirety.

FIELD

This invention relates generally to rechargeable electric batteries particularly suited for applications, e.g., implanted medical devices, where a battery cannot be easily replaced. More particularly, the invention relates to rechargeable lithium batteries configured to tolerate deep discharging to zero volts without permanently damaging the battery's energy storing capacity.

BACKGROUND

Rechargeable electric batteries are employed in a wide range of applications, e.g., consumer products, medical devices, and aerospace/military systems, which respectively impose different performance requirements. In some applications, e.g., implanted medical devices, it is important that the battery be able to reliably maintain its performance characteristics over a long useful life despite extended periods of inactivity. Implanted medical device applications impose special requirements on a battery because the medical device needs to be highly reliable to perform critical tasks, the battery may remain inactive and uncharged for extended periods, e.g., several months, and it is difficult and/or expensive to replace a battery. Analogous conditions exist in various aerospace/military applications. For example, a rechargeable battery may be deployed to power a satellite in deep space where it cannot be replaced and must be able to operate over a long life under varying conditions, including long periods of inactivity. Military applications often demand similar performance specifications since military hardware can be unused for several months but must remain ready to be activated. Current battery technology requires stored batteries to be charged every few months to avoid a permanent reduction in energy storing capacity.

In order to avoid unnecessary surgery to replace a damaged battery in an implanted medical device, it is desirable that a battery perform reliably over a very long life, i.e., several years, under a variety of conditions. Such conditions can include extended periods of non-use which may allow the battery to deeply self discharge to zero volts. It is typical for prior art rechargeable lithium batteries to suffer a permanent capacity loss after discharging below 2.5 volts. To avoid such capacity loss, it is important to regularly charge prior art lithium batteries.

Existing rechargeable lithium batteries typically consist of a case containing a positive electrode and a negative electrode spaced by a separator, an electrolyte, and feedthrough pins respectively connected to the electrodes and extending externally of the case. Each electrode is typically formed of a metal substrate that is coated with a mixture of an active material, a binder, and a solvent. In a typical battery design, the electrodes comprise sheets which are rolled together, separated by separator sheets, and then placed in a prismatic or cylindrical case. Positive and/or negative feed through pins (i.e., terminals) are then connected to the respective electrodes and the case is filled with electrolyte and then sealed. The negative electrode is typically formed of a copper substrate carrying graphite as the active material. The positive electrode is typically formed of an aluminum substrate carrying lithium cobalt dioxide as the active material. The electrolyte is most commonly a 1:1 mixture of EC:DEC in a 1.0 M salt of $LiPF_6$. The separator is frequently a microporous membrane made of a polyolephine, such as a combination of polyethylene and/or polypropylene which can, for example, be approximately 25 microns thick.

Batteries used in implanted medical devices can be charged from an external power source utilizing a primary coil to transfer power through a patient's skin to a secondary coil associated with the implanted medical device. The secondary coil and an associated charging circuit provide a charging current to the battery. Protection circuitry is typically used in conjunction with prior art lithium batteries to avoid the potential deleterious effects of over or under charging the battery. Such protection circuitry can terminate charging if the voltage or temperature of the battery exceeds a certain level. Moreover, it is common to also incorporate low voltage protection to disconnect the battery from its load if the voltage of the battery falls below a certain lower level. This latter precaution is taken to prevent permanent damage to the battery that will likely occur if the voltage on an electrode exceeds a Damage Potential Threshold (DPT). For example, it is well known in the industry that discharging a lithium battery to below 2.5 volts and storing it for an extended period of time will likely result in a permanent loss of battery capacity. Despite incorporating low voltage cutoff protection to disconnect the battery from its load if the voltage falls below a certain threshold, typical prior art batteries will slowly self-discharge further causing the voltage of an electrode to exceed the Damage Potential Threshold.

SUMMARY

The present invention is directed to a rechargeable lithium battery particularly configured to permit it to discharge to a very low voltage, e.g. zero volts, without causing permanent damage to the battery. More particularly, a battery in accordance with the invention is configured to define a Zero Volt Crossing Potential (ZCP) which is lower than the battery's Damage Potential Threshold (DPT).

ZCP refers to the voltage on the positive and negative electrodes relative to a lithium reference (Li/Li+) when the battery potential, i.e., the voltage between the electrodes, is zero. The Damage Potential Threshold (DPT) is attributable to at least two factors, i.e., a Substrate Dissolution Potential (SDP) and a Film Dissolution Potential (FDP). SDP refers to the voltage of the negative electrode, relative to the lithium reference, above which the electrode substrate starts to corrode or decompose to permanently damage the substrate. FDP refers to the voltage of the negative electrode, relative to the lithium reference, above which a solid electrolyte interface (SEI) layer begins to dissolve. The SEI, or film, comprises a passivation layer which, in normal operation, forms on the negative electrode and functions to inhibit a continuing reaction between the negative electrode active material and the electrolyte. When the voltage of the negative electrode relative to the lithium reference, exceeds either SDP or FDP, physical damage to the electrode is likely to occur thereby permanently impairing the battery's capacity.

A battery's ZCP level relative to the lithium reference is dependent in part on the materials used for the positive and/or negative electrodes. In accordance with a preferred embodiment of the invention, a positive electrode active material $LiNi_xCo_{1-x}O_2$ is selected which exhibits a discharge voltage curve appropriate to achieve a relatively low Zero Crossing Potential (ZCP) level. This feature of the preferred embodiment facilitates the implementation of a battery characterized by a ZCP less than its Damage Potential Threshold (DPT). It has been recognized that as more Ni is substituted for Co (i.e., increasing x), the magnitude of the discharge voltage profile decreases. It has been determined that values of x between 0.5 and 1.0 optimally achieve the desired ZCP/DPT relationship in accordance with the present invention, i.e., $LiNi_xCo_{1-x}O_2$ (where $0.5 \leq x \leq 1.0$). For $x<0.5$, there is a noticeable degradation in capacity retention after storage at zero volts indicating that some corrosion or internal battery degradation has occurred at low voltage similar to the results seen from a conventional lithium battery design.

In accordance with a preferred embodiment of the invention, $LiNi_{0.8}Co_{0.2}O_2$ is used for the positive active material on a thin metal substrate, e.g., aluminum. The negative electrode is preferably formed of a titanium or titanium alloy substrate carrying a layer of negative active material, e.g., graphite coated on both faces of the substrate.

Batteries in accordance with the present invention are particularly suited for use in critical applications where physical access to the battery is difficult and/or expensive, such as in medical devices configured to be implanted in a patient's body. Such a medical device is typically comprised of a hermetically sealed housing formed of biocompatible material and dimensioned to be implanted without interfering with normal body function. A battery in accordance with the invention includes a case configured for mounting in the device housing. The battery case can be of a variety of shapes, e.g., prismatic or cylindrical, and typically defines a volume of between 0.05 cc and 30 cc. Batteries within this range exhibit capacities between 1.0 milliamp hours and 10 amp hours. An exemplary battery for use in a neurostimulation device includes a prismatic hermetically sealed battery casing having dimensions of 35 mm×17 mm×5.5 mm. A wide variety of medical device applications are discussed in the medical and patent literature; see, for example, U.S. Pat. No. 6,185,452.

BRIEF DESCRIPTION OF THE FIGURES

The above and other features and uniqueness of the invention will be better visualized from the following drawings and schematics.

DESCRIPTION

A rechargeable battery in accordance with the present invention is particularly suited for use in medical devices intended to be implanted in a patient's body. Such medical devices are extensively discussed in the medical and patent literature. For example, U.S. Pat. No. 6,1895,452 describes a Battery-Powered Patient Implantable Device utilizing a rechargeable battery depicted in alternative constructions in FIGS. 8A through 8G. The present invention is directed to an improved rechargeable lithium battery, useful in devices of the type described in U.S. Pat. No. 6,185,452, configured to tolerate deep discharging without significantly impairing the battery's ability to recover its original storage capacity.

Figure 1A:
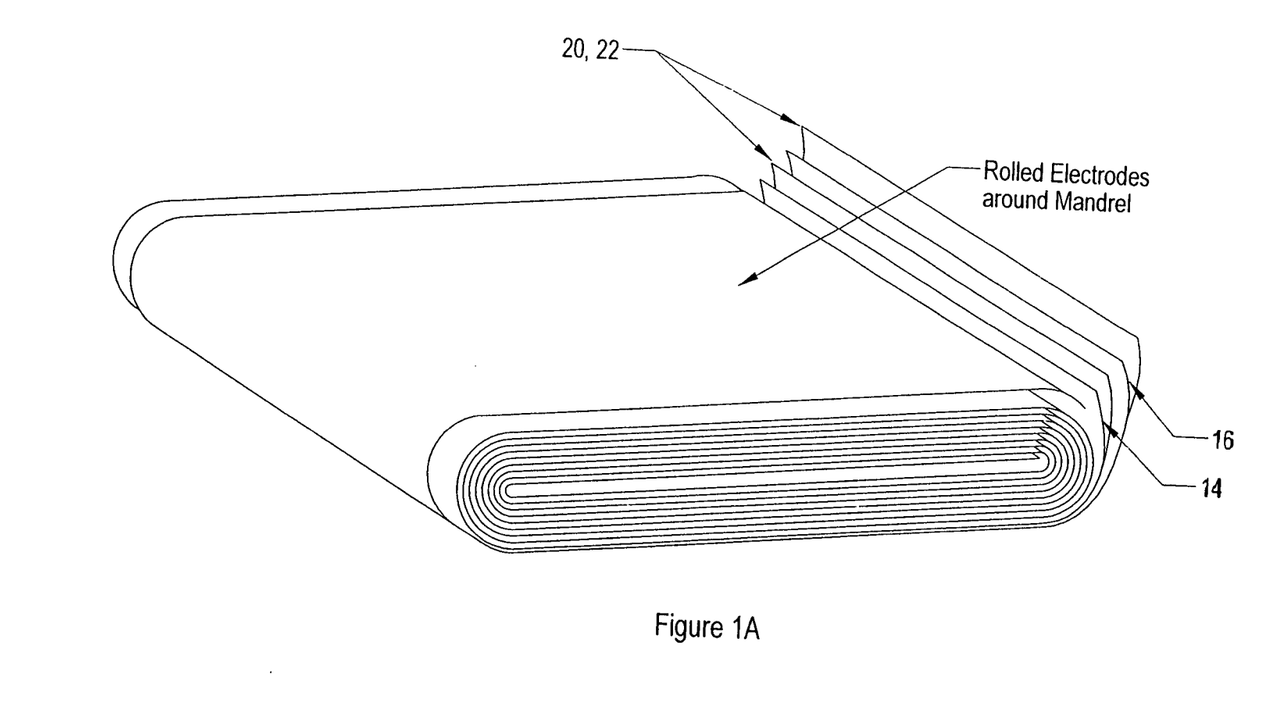
FIG. 1A schematically depicts positive and negative battery electrodes rolled around a mandrel for placement in a battery case and FIG. 1B depicts in cross-section a complete battery.
Figure 1B:
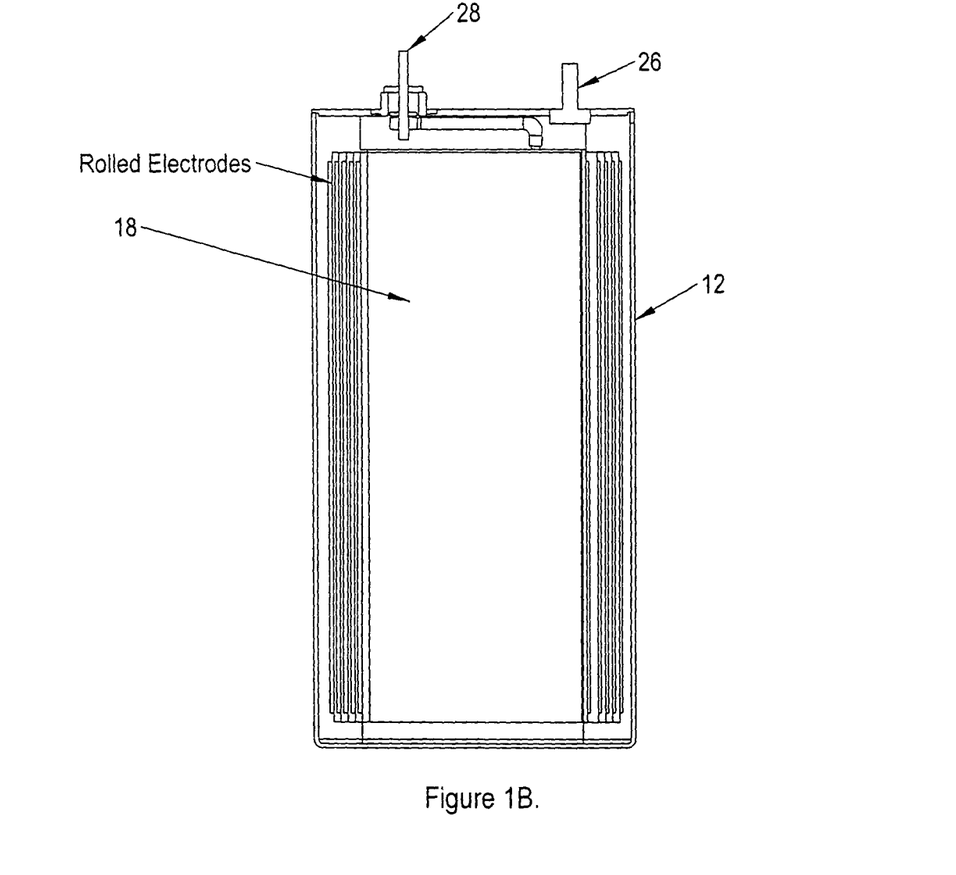

FIGS. 1A and 1B schematically depict a typical lithium battery construction 10 comprising a prismatic case 12 containing a positive electrode 14 and a negative electrode 16, rolled around a mandrel 18. Separator sheets 20, 22 are incorporated in the rolling to electrically separate the electrodes. The case 12 also typically includes electrolyte material (not shown) and positive and negative feed through pins (i.e., terminals) 26, 28 which are respectively connected to the electrodes 14, 16 and extend externally of the case 12.

Typical prior art lithium ion batteries include a positive electrode 14 comprised of a thin metal substrate, e.g., aluminum, carrying a layer of positive active material, e.g., lithium cobalt dioxide $LiCoO_2$ mixed with a binder, and coated on both faces of the substrate. The negative electrode 16 is typically comprised of a thin metal substrate, e.g., copper, carrying a layer of negative active material, e.g., graphite coated on both faces of the substrate.

Two layers of separator 20, 22 electrically separate the electrodes 14, 16 from each other, enabling the electrodes to be rolled around mandrel 18. Each separator layer can comprise a micro porous membrane made of a combination of polypropylene and is approximately 25 μm thick. The electrolyte is most commonly a 1:1 mixture of EC:DEC in a 1.0 M salt of $LiPF_6$.

Figure 2:
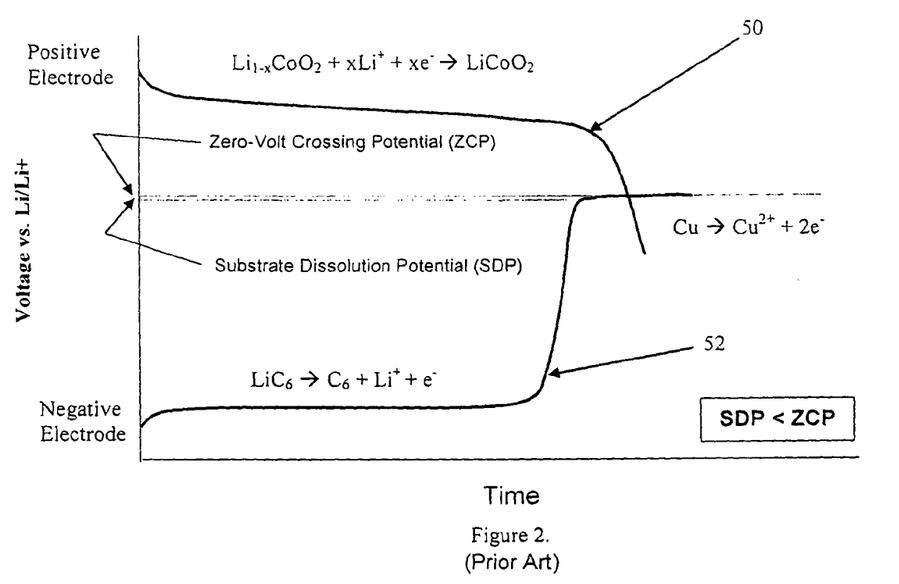
FIG. 2 shows a typical deep discharge curve for a conventional lithium ion battery using copper as the negative electrode substrate and lithium cobalt dioxide LiCoO2 as the positive electrode active material.

FIG. 2 shows typical deep discharge performance curves for a conventional lithium ion battery. The y-axis represents voltage relative to a lithium reference (Li/Li+) or counter electrode and the x-axis represents time. Curves 50 and 52 respectively depict the discharge curves for the positive and negative electrodes. The battery output voltage is the difference between the positive electrode voltage and the negative electrode voltage. During discharge, the positive electrode voltage decreases relative to the lithium reference and the negative voltage increases, primarily near the end of discharge. A protection or management circuit (not shown) is typically provided to disconnect the load to stop the discharge when the battery voltage reaches 2.5 volts. If, however, the discharge continues (attributable, for example, to self-discharge over a long period of time), the negative electrode potential will rise until it reaches the potential of the positive electrode. This constitutes the Zero Volt Crossing Potential (ZCP) and is typically about 3.6 volts in conventional lithium ion battery constructions. The negative electrode potential at ZCP can exceed the Substrate Dissolution Potential (SDP) of the negative electrode substrate, e.g., 3.3 volts for copper, and cause decomposition and permanent damage to the substrate. The present invention is directed to battery improvements to assure that the value of SDP is greater than the value of ZCP, as represented in FIG. 3.

Figure 3:
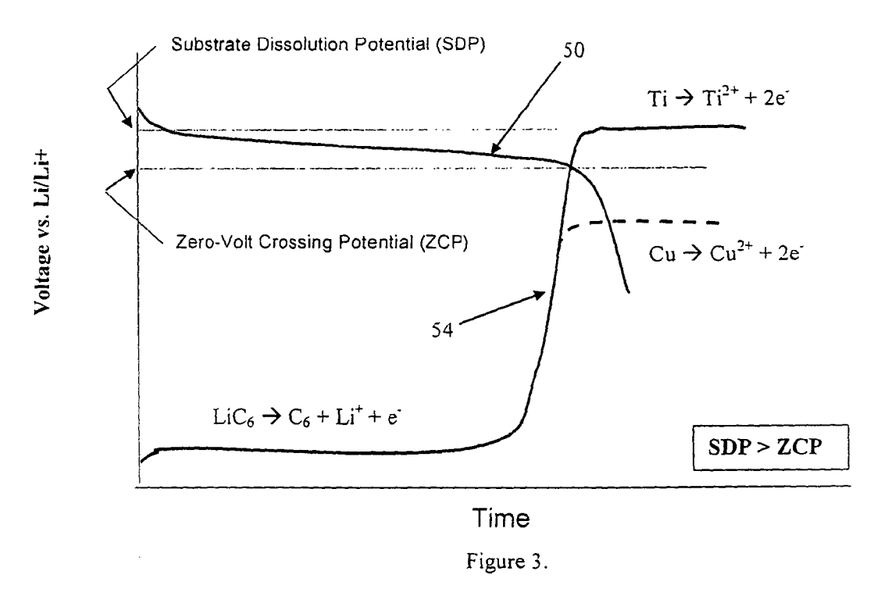
FIG. 3 shows a typical deep discharge curve for a lithium ion battery in accordance with the present invention using titanium as the negative electrode substrate.

FIG. 3 depicts deep discharge performance curves for a lithium battery in accordance with the present invention in which the negative electrode substrate is formed of titanium instead of copper. The use of titanium increases the knee of the negative electrode curve 54 to position the SDP level above the ZCP level. This relationship considerably reduces potential damage to the negative electrode substrate. In addition to commercially pure titanium, i.e., titanium CP, other materials can be used to raise the SDP sufficiently, e.g. titanium alloys, nickel, nickel alloys, and stainless steel.

FIG. 3 demonstrates how the SDP level can be increased relative to the ZCP by proper choice of the negative electrode substrate material. Alternatively, or additionally, the ZCP level can be decreased relative to the SDP by proper choice of the positive electrode active material, as depicted in FIG. 4.

Figure 4:
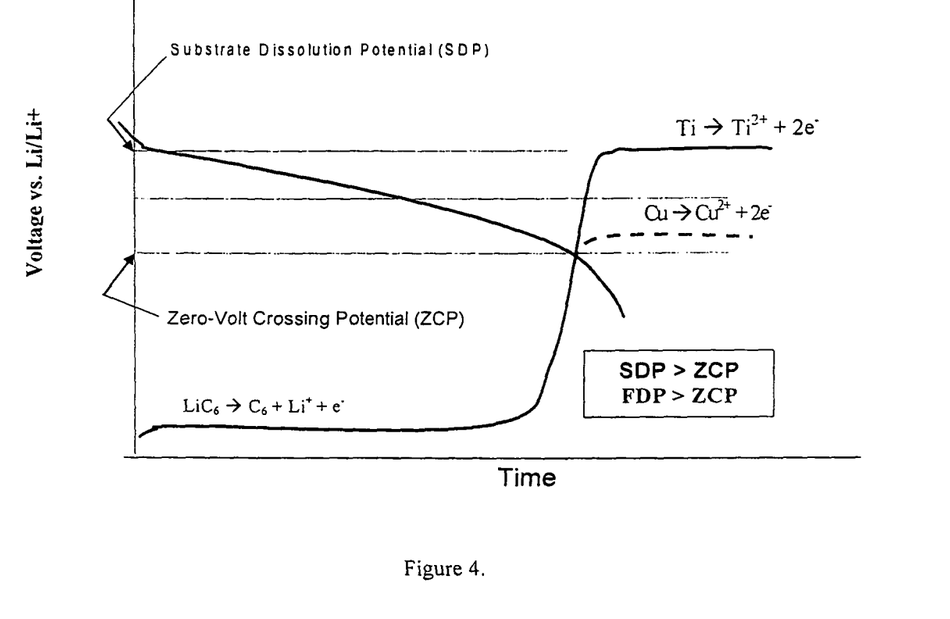
FIG. 4 shows a typical deep discharge curve for a lithium ion battery in accordance with the present invention using $LiNi_xCo_{1-x}O_2$ ($0.5 \leq x \leq 1.0$) as the positive electrode active material.

More particularly, FIG. 4 shows the discharge curve 60 for a positive electrode using lithium nickel cobalt dioxide $LiNi_xCo_{1-x}O_2$ (where $0<x\leq 1$) as the active material, i.e., as the intercalation compound. Note that the curve of FIG. 4 exhibits a greater negative slope than the analogous curve 50 of FIG. 2 representing the standard intercalation compound $LiCoO_2$. The effect of the increased negative slope is to lower the ZCP level relative to the lithium reference and the SDP. As was the case in connection with FIG. 3, this reduces the potential damage to the negative electrode substrate. Additionally, however, the ZCP level also falls below a Film Dissolution Potential (FDP) which is the voltage above which a solid electrolyte interface (SEI) layer begins to dissolve. The SEI, or film, comprises a passivation layer which forms on the negative electrode and functions to inhibit a continuing reaction between the negative electrode active material and the electrolyte. Dissolution of the SEI can noticeably damage the negative electrode active material.

Experiments have been performed at two different temperatures employing the aforedescribed techniques depicted in FIGS. 3 and 4. The preliminary results are summarized in the table of FIG. 5. Four different battery configurations were constructed as shown. Configuration (1) corresponds to the conventional arrangement represented in FIG. 2 comprising a copper substrate for the negative electrode and $LiCoO_2$ for the positive active material. The battery was built and then recycled once to get an initial capacity measurement. The battery was then shorted between the positive and negative leads to achieve a zero volt state. This zero volt condition was held for one week and then recharged and discharged to get a capacity measurement after zero-volt storage. The capacity retention is calculated by dividing the discharge capacity after zero volt storage by the initial capacity and multiplying by 100%. In this manner, this percentage reflects any damage that had occurred to the battery while in the zero volt state.

Figure 5:
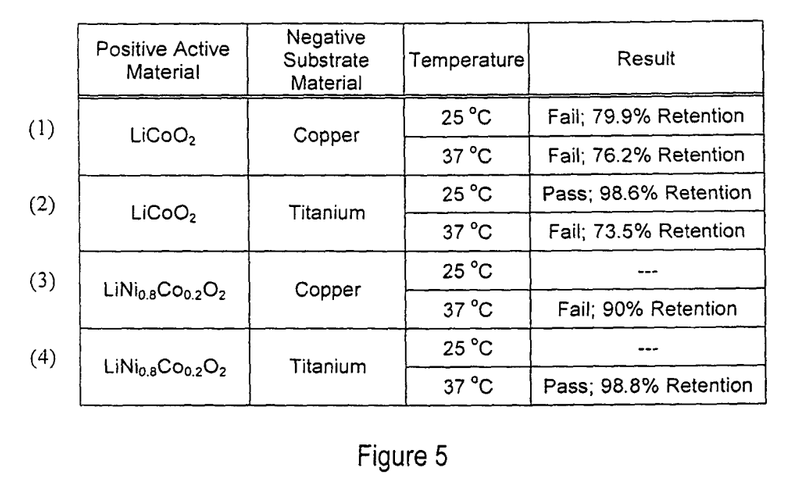
FIG. 5 is a table showing test results of various battery configurations including a preferred embodiment in accordance with the present invention.

As represented in FIG. 5, the capacity retention for battery configuration (1) is below 80%, thus suggesting that the zero volt condition had significantly damaged the battery. After opening the battery and examining the electrodes, it was seen that dissolution of the negative electrode copper substrate had occurred. This battery (1) configuration performed poorly at both temperature settings.

The battery configuration (2) used $LiCoO_2$ as the positive active material and a titanium substrate as the negative substrate corresponding to the arrangement represented in FIG. 3. The results show that at 25° C. the capacity retention was at about 98% after the zero volt condition. However, at a higher temperature (37° C.) exemplary of medical implant conditions, performance deteriorates to below 80%. This suggests that perhaps the zero volt crossing potential was sufficiently below SDP to avoid substrate dissolution but still high enough to exceed FDP and cause damage to the negative electrode active material. Accordingly, attempts were made to lower ZCP further to avoid damage both to the negative active material and the negative electrode substrate.

The battery configuration (3) utilizes $LiNi_xCo_{1-x}O_2$ (where x=0.8) as the positive electrode active material and a conventional copper negative electrode substrate. The results show that at 37° C., the capacity retention is quite high at 90%. However, examination after the test, revealed that some dissolution of the copper substrate had occurred. Battery configuration (4) uses both $LiNi_{0.8}Co_{0.2}O_2$ as the positive active material and titanium as the negative electrode substrate material. Results show that this configuration gives the best capacity retention after zero volt storage.

From the curves of FIG. 4 and the table of FIG. 5, it appears that some performance gain is achieved by configuration (2) using a titanium negative electrode substrate and by configuration (3) using $LiNi_xCo_{1-x}O_2$ (where x=0.8) as the positive active material. However, maximum performance gain appears in configuration (4) which combines both of these features.

Figure 6:
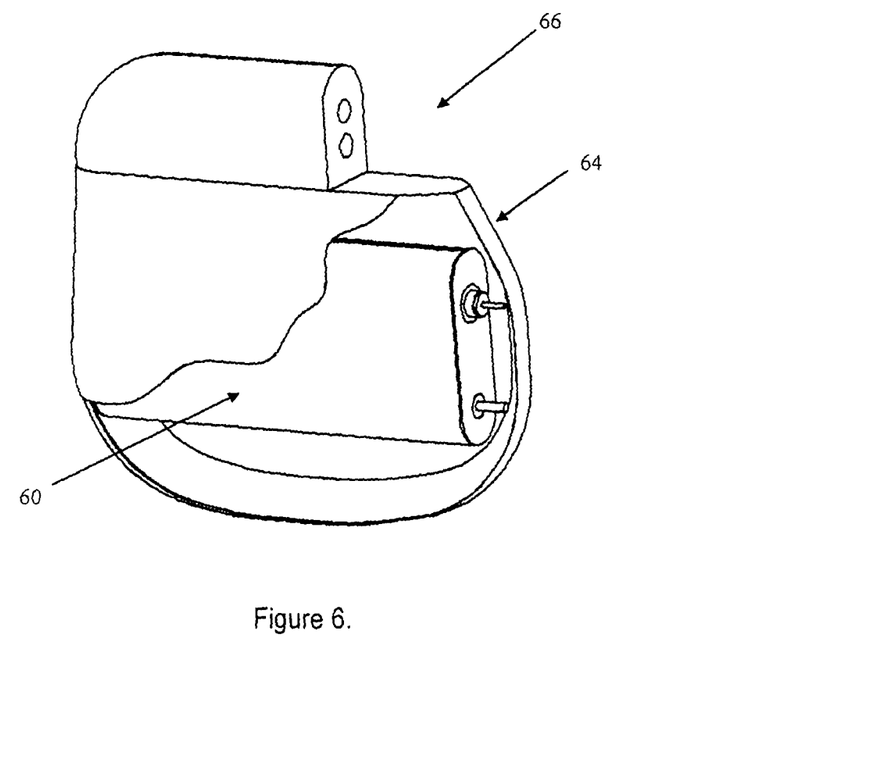
FIG. 6 schematically depicts a battery in accordance with the invention contained within an implantable medical device housing.

FIG. 6 schematically depicts a battery 60 in accordance with the invention mounted in a housing 64 (shown partially open for the purposes of illustration) of a medical device 66 configured for implanting in a patient's body. The housing 64 is preferably formed of biocompatible material and hermetically sealed. The device 66 is typically used for monitoring and/or affecting body parameters. For example, the device can be used to electrically stimulate nerves. The casing 68 of battery 64 can, for example, have dimensions of 35 mm×17 mm×5.5 mm. Other configurations and sizes are suggested in the literature, e.g., U.S. Pat. No. 6,185,452.

While the invention has been described with reference to specific exemplary embodiments and applications, it should be recognized that numerous modifications and variations will occur to those skilled in the art without departing from the spirit and scope of the invention set forth in the appended claims.

We claim:

1. A method of manufacturing a battery, comprising:
   providing a positive electrode and a negative electrode, said positive electrode comprising a metal substrate having a first active material comprising lithium formed thereon and said negative electrode comprising a metal substrate having a second active material comprising carbon formed thereon, wherein said positive and negative electrodes define a Zero Volt Crossing Potential (ZCP) relative to a reference level when the voltage between said electrodes is zero;
   providing an electrolyte wherein said negative electrode can react with said electrolyte to form a solid electrolyte interface (SEI) layer, said SEI layer being susceptible of damage when a voltage potential exceeding a Film Dissolution Potential (FDP) is applied thereto, and wherein said FDP is lower than the maximum positive operating potential of the battery; wherein said positive and negative electrodes are selected to establish ZCP at a lower level than FDP to prevent dissolution of said SEI layer during storage at a predetermined temperature.

2. The method of claim 1, wherein said negative electrode substrate is susceptible of permanent damage when a potential exceeding a Substrate Dissolution Potential (SDP) is applied thereto; and wherein said positive and negative electrodes are selected and configured to establish ZCP at a lower level than SDP in order to prevent dissolution of the negative substrate during storage at said predetermined temperature.

3. The method of claim 1, wherein said negative electrode substrate is formed of a material selected from the group consisting of titanium and titanium alloy.

4. The method of claim 1, wherein said negative electrode substrate is formed of stainless steel.

5. The method of claim 1, wherein said negative electrode substrate is formed of a material selected from the group consisting of nickel and nickel alloy.

6. The method of claim 1, wherein said positive electrode active material comprises cobalt.

7. The method of claim 6, wherein said positive electrode active material further comprises nickel.

8. The method of claim 1, wherein said positive electrode active material consists of an oxide.

9. The method of claim 8, wherein said oxide comprises lithium, nickel, and cobalt.

10. The method of claim 1, wherein said negative electrode active material consists of carbon.

11. The method of claim 1, wherein said electrolyte consists of a liquid electrolyte.

12. The method of claim 11, wherein said liquid electrolyte comprises a lithium salt dissolved in EC:DEC.

13. The method of claim 12, wherein said lithium salt is $LiPF_6$.

14. The method of claim 1, wherein said predetermined temperature is body temperature.

15. The method of claim 1, wherein said predetermined temperature is 37° C.

16. The method of claim 1, wherein said predetermined temperature is 25° C.

17. The method of claim 1, further comprising providing a battery management circuit that attempts to stop battery discharge when the battery voltage reaches 2.5 V.

18. The method of claim 1, wherein said ZCP is greater than about 3 V vs. $Li/Li^+$.

19. The method of claim 1, wherein said positive electrode has a positive discharge curve having a negative slope over most of said positive discharge curve, wherein said negative slope is more negative than the negative slope over most of the discharge curve of $LiCoO_2$.

20. The method of claim 1, further comprising the step of:

housing said positive and negative electrodes in a case, wherein said case is configured for implanting in a patient's body.

21. The method of claim 20, further comprising the step of:

hermetically sealing the case.

22. The method of claim 20, wherein said case has a volume of less than 30 cc.

23. A method for making a rechargeable lithium ion battery comprising:

providing a positive electrode comprising a metal substrate having a first active material comprising lithium formed thereon;

providing a negative electrode comprising a substrate selected from the group consisting of titanium and titanium alloy having a second active material comprising carbon formed thereon;

said negative electrode being susceptible of damage when a voltage exceeding a Damage Potential Threshold (DPT) is applied thereto, and wherein said DPT is lower than the maximum positive operating potential of the battery;

said positive and negative electrodes defining a Zero Volt Crossing Potential (ZCP) relative to a reference level when the voltage between said electrodes is zero; and wherein said positive and negative electrodes are selected and configured to define a value of ZCP which is less than the value of DPT at a predetermined temperature.

24. The method of claim 23, wherein the first active material comprises cobalt.

25. The method of claim 24, wherein the first active material further comprises nickel.

* * * * *